United States Patent [19]

Pagano

[11] 4,165,648
[45] Aug. 28, 1979

[54] TWO WHEEL ULTRASONIC RAIL TESTING SYSTEM AND METHOD

[76] Inventor: Dominick A. Pagano, 10 Sasqua Trail, Georgetown, Conn. 06829

[21] Appl. No.: 818,544

[22] Filed: Jul. 25, 1977

[51] Int. Cl.² ............................................ G01N 29/04
[52] U.S. Cl. ...................................... 73/625; 73/636; 73/639
[58] Field of Search ................. 73/599, 618, 620, 621, 73/624–626, 628, 629, 636, 639

[56] References Cited

U.S. PATENT DOCUMENTS

| | | | |
|---|---|---|---|
| 2,799,157 | 7/1957 | Pohlman | 73/624 X |
| 2,893,239 | 7/1959 | Renaut | 73/625 X |
| 3,028,751 | 4/1962 | Joy | 73/636 X |
| 3,251,220 | 5/1966 | Joy | 73/625 X |
| 3,257,843 | 6/1966 | Cowan | 73/639 |
| 3,415,110 | 12/1968 | Cowan | 73/628 X |
| 3,442,119 | 5/1969 | Cowan | 73/639 |
| 3,548,644 | 12/1970 | O'Connor et al. | 73/626 X |
| 3,962,908 | 6/1976 | Joy | 73/636 |

OTHER PUBLICATIONS

"Nondestructive Testing Handbook", by McMaster, pp. 44-12 to 44-27, Ronald Press Co., N.Y. —1959.

*Primary Examiner*—James J. Gill
*Attorney, Agent, or Firm*—St. Onge, Steward, Johnston, Reens & Noe

[57] ABSTRACT

A system and method for performing ultrasonic inspection of a length of test material with ultrasonic transducing means emitting a beam of ultrasonic energy from within sealed wheel means containing a coupling fluid therein and having a flexible cylindrical surface member transparent to the ultrasonic beam and arranged for rolling contact along the test material. The system and method are characterized by spaced leading and trailing wheel means arranged for rolling contact along the length of test material. Ultrasonic transducer means in each of the leading and trailing wheel means are oriented so that a beam of ultrasonic energy emitted from the transducer means in one wheel means will enter the test material, be reflected from the bottom surface thereof, and be directed to and received by the transducer means in the other wheel means. Each wheel means further includes ultrasonic transducers emitting ultrasonic energy longitudinally in front of and behind the two wheels, and side-looking transducer means for emitting ultrasonic energy into the test material transversely to the direction of travel. Additional transducers emit radiation perpendicularly through the test material. Accordingly, the test material is fully probed and many different kinds of defects can be detected. The transducers are positioned away from the test material by a distance which is substantially the near field distance of the ultrasonic beam. Means are provided for adjusting the spacing between two wheels to allow different thicknesses of test material to be tested by interwheel transmission of the ultrasonic beam.

47 Claims, 8 Drawing Figures

TWO WHEEL ULTRASONIC RAIL TESTING SYSTEM AND METHOD

BACKGROUND OF THE INVENTION

1. Field of the Invention

This invention relates to systems and methods for the ultrasonic inspection of a length of test material such as a railroad rail and, more specifically, to ultrasonic inspection performed with ultrasonic transducing means emitting a beam of ultrasonic energy from within sealed wheel means containing a coupling fluid therein and having a flexible cylindrical surface member transparent to the ultrasonic beam and arranged for rolling contact along the test material.

2. Description of the Prior Art

Various ultrasonic inspection units are known to the art for rolling contact with a length of material to be tested. One particularly advantageous example of an ultrasonic testing apparatus, disclosed in my U.S. Pat. No. 3,628,375, has enabled rail testing to be performed rapidly and with more reliable detection of defects. Despite this advance, however, still more enhanced performance is desirable to detect a wider variety of defects and smaller defects.

SUMMARY OF THE INVENTION

A principal object of the present invention is to provide an improved system and method for performing ultrasonic inspection of a length of test material. A particular object of the invention is to provide such a system and method which are more sensitive to defects in the test material, are capable of detecting a wider variety of defects, and which are adaptable easily to a number of different test materials, such as different sizes of rails. Still another object of the invention is to provide a system and method for ultrasonic inspection which are more suitable for commercial use.

In a particular embodiment of the invention to be described hereinbelow in detail, the system and method are of the type for performing ultrasonic inspection of a length of test material, such as a rail, with ultrasonic transducing means emitting a beam of ultrasonic energy from within sealed wheel means containing a coupling fluid therein and having a flexible cylindrical surface member transparent to the ultrasonic beam and arranged for rolling contact along the test material. In accordance with the invention, leading and trailing wheel means are arranged for rolling contact along the length of test material. In each of the leading and trailing wheel means, ultrasonic transducer means are oriented so that a beam of ultrasonic energy emitted from the transducer means in one wheel means will enter the test material, be reflected from the bottom surface thereof, and be directed to and received by the transducer means in the other wheel means. A reading of the transmitted energy will indicate whether energy has been deflected away from the receiving transducer by defects in the test material. In more detailed aspects of the invention, the interwheel transducer means are arranged to alternately transmit and receive. The spacing between the leading and trailing wheel means is adjusted to permit ultrasonic energy to be beamed from one wheel to another through different thicknesses of test material. In addition, the interwheel transducers are positioned so that the ultrasonic beam makes a transition from the near field mode to the far field mode where it enters the test material.

In other aspects of the invention, the leading and trailing wheel means are also provided with longitudinally-looking transducer means for emitting a beam of ultrasonic energy into the test material in advance of and behind the moving wheel means, e.g., at an angle of 70° to a perpendicular to the test material surface. In addition, side-looking transducer means emit ultrasonic radiation transversely to the direction of wheel travel, e.g., with the leading wheel emitting radiation to one side, and the trailing wheel emitting radiation to the other side. Further transducers in each wheel means emit radiation perpendicularly to the test material. In one preferred embodiment of the invention, the spacing between the leading and trailing wheel means is adjusted in response to a thickness measurement of the test material taken with a transducer emitting an ultrasonic beam perpendicularly through the test material.

In still other aspects of the invention, each wheel means is provided with circular flange means internally of the flexible cylindrical surface member and carrying resilient O-rings on their outer periphery to engage the test material through the flexible cylindrical surface member and thereby accurately space the transducer means from the test material. The flexible cylindrical cover, which fits around the exterior of the flange means and is secured thereto, is free to conform to the surface of the test material and provides a large contact area for coupling of the various ultrasonic beams into the test material.

Other objects, aspects and advantages of the invention will be pointed out in, or apparent from, the detailed description hereinbelow, considered together with the following drawings.

DESCRIPTION OF THE PREFERRED EMBODIMENT

FIGS. 1 through 5 illustrate a two wheel ultrasonic inspection system 10 arranged to detect flaws and defects in a length of test material M, illustrated as a rail having a substantially rectangular head 12 with an upper surface 13, a vertical web 14, and a base 16 with a bottom surface 17 typically resting on ties (not shown).

Figure 1:
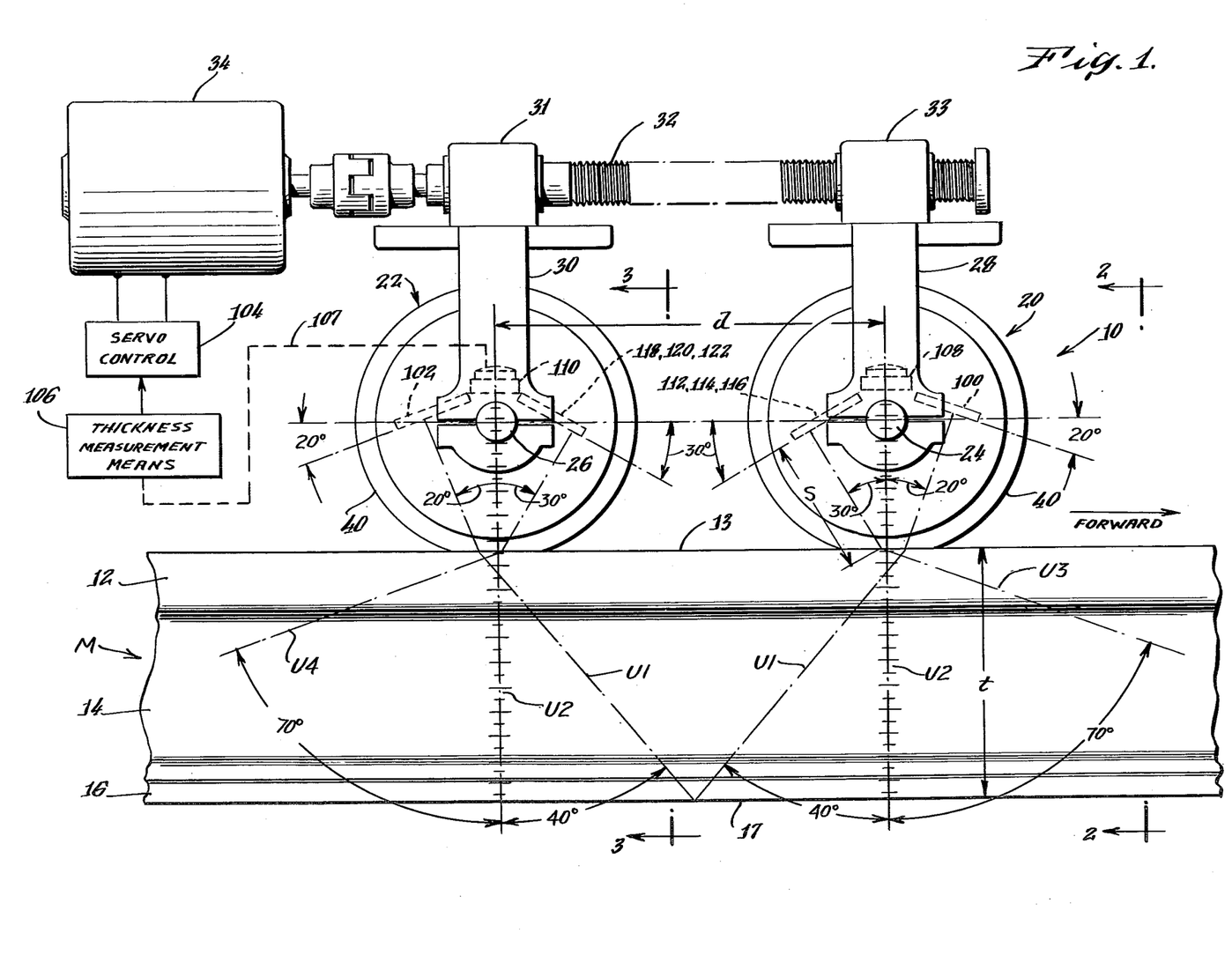
FIG. 1 is a side elevational view of an ultrasonic inspection system in accordance with the present invention.

Arranged for rolling contact along the upper surface 13 of rail head 12 are a leading test wheel 20 and a trailing test wheel 22 separated by a distance d. The wheels 20 and 22 rotate about fixed shafts 24 and 26 secured respectively to support arms 28 and 30 which are spring loaded downward by conventional means upon a carriage (not shown) which propels the wheels along the length of test material M. As shown in FIG. 1, the support arms 28 and 30 are interconnected by means of a lead screw 32 journaled into bearing means 31 in support arm 30 and threadably engaging a screw threaded socket 33 in support arm 28 and rotated by a motor 34 to adjust the spacing distance d between the leading wheel 20 and trailing wheel 22.

Figure 2:
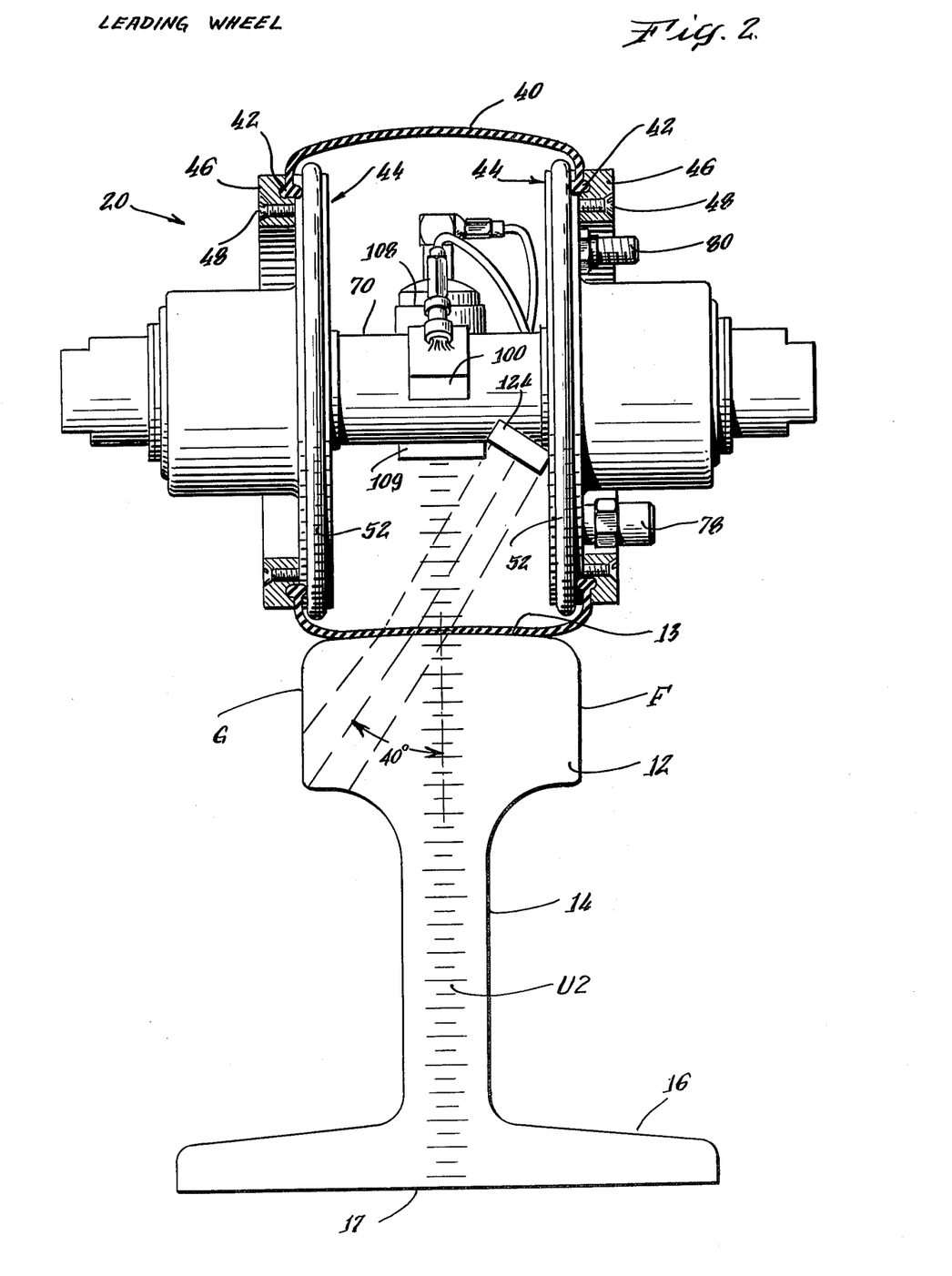
FIG. 2 is a section on line 2—2 of FIG. 1.
Figure 3:
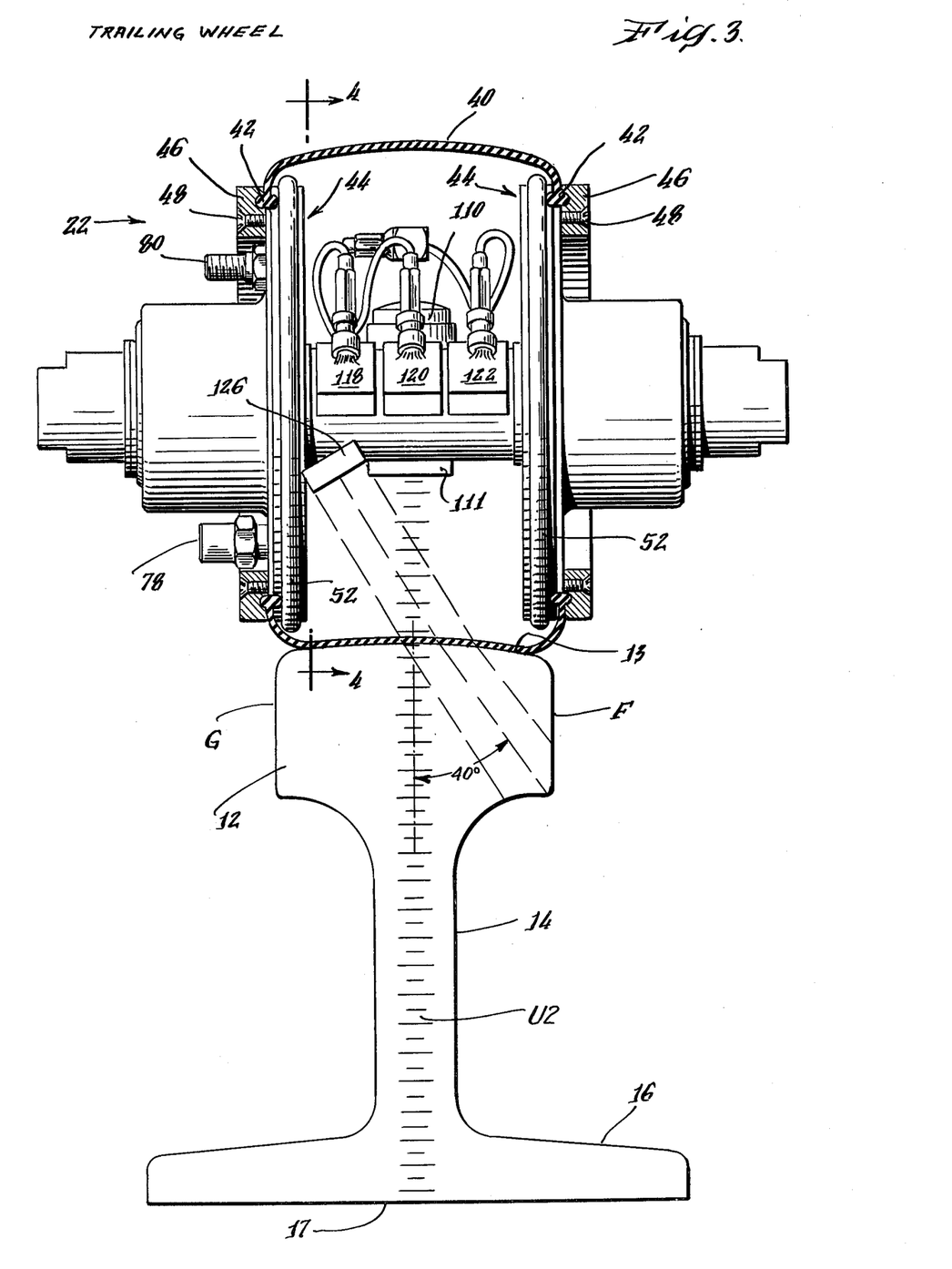
FIG. 3 is a section on line 3—3 of FIG. 1.
Figure 4:
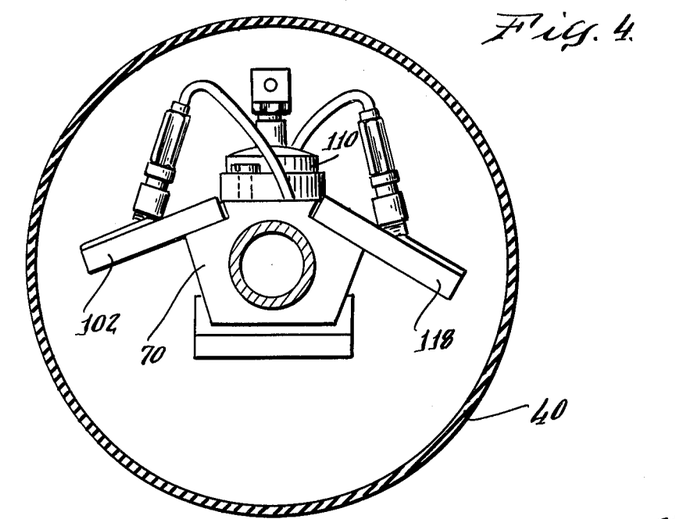
FIG. 4 is a section on line 4—4 of FIG. 3.
Figure 5:
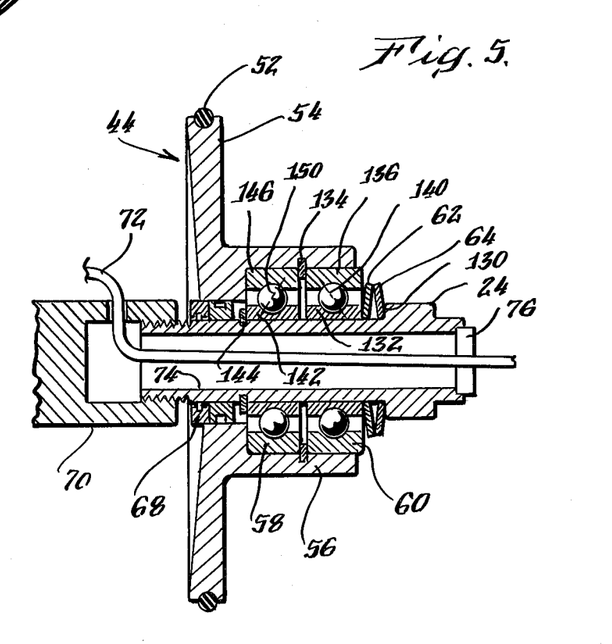
FIG. 5 is a radial section of a flange arrangement according to the invention.

As shown in FIGS. 2 and 3, the leading wheel 20 and trailing wheel 22 are each constructed with a flexible cylindrical surface member 40 made, for example, from a high durometer urethane membrane, which is transparent both visually and ultrasonically. The cylinder surface member 40 is provided with outer beads 42 which are clamped in opposed circular grooves in flange members 44 and clamping rings 46 secured to the flange members by screws 48. The flange members 44, as shown in FIG. 5, have a circular peripheral groove 50 seating a circumferential rubber O-ring 52. The O-ring 52, which is located internally of the cylindrical surface member 40, is arranged to press down on the upper surface 13 of the test material M through the flexible member 40 (FIGS. 2 and 3) to accurately space the axes of wheels 20 and 22 from the upper surface 13 of the test material M. As will be explained below, this provides predetermined path distances for ultrasonic beams emitted by transducers mounted within the wheels, and improves inspection capabilities. In FIGS. 2 and 3, for purposes of illustration, the rings 52 are shown slightly away from pressing the flexible member 40 down fully onto surface 13.

As shown in FIG. 5, the flange member 44 comprises a disc portion 54 integral with a hub portion 56 which is rotatably connected to one of the fixed shafts 24 (or 26) by means of preloaded double bearings 58 and 60 with spring pressure applied axially thereto through opposed Bellville washers 62 and 64. A fluid seal between fixed shaft 24 and flange member 44 is achieved with a magnetic seal 68, such as that commercially available from Magnetic Seal Corporation, West Barrington, R.I. At its inner end, fixed shaft 24 threadably engages a transducer mounting yoke 70 which carries ultrasonic transducers in a manner to be described below. Signal cables 72 for the ultrasonic transducers are led externally of the testing wheels 20 and 22 through a bore 74 in shaft 24 and through a fluid seal 76. As shown in FIGS. 2 and 3, fluid fill and air bleed check valves 78 and 80 are provided in the disc portions 54 of flange members 44. The sealed interior portions of leading wheel 20 and trailing wheel 22 are filled with an ultrasonic coupling fluid, composed for example of water, glycol, or a mixture thereof such as 40% glycol and 60% water.

As illustrated in FIG. 1, the mounting yoke 70 of the leading wheel 20 carries a rearward-looking ultrasonic transducer 100 which is oriented to emit a beam of ultrasonic energy U1 (shown by a dashed line) which travels through the coupling fluid within wheel 20 and through the flattened region where cylindrical surface 40 contacts the upper surface 13 of test material M. This transducer 100 may preferably be a crystal transducer having an active area ½ of an inch wide and ¾ of an inch long as measured along its inclined direction, as seen in FIG. 1.

The beam of ultrasonic energy is refracted in accordance with Snell's law due to the different propagation velocities of the beam in the wheel fluid and in the steel rail, and travels to the bottom surface 17 of the test material M where it is reflected upwardly and travels through the rail to the flattened region of the other wheel membrane where the cylindrical surface 40 of trailing wheel 22 contacts the test member. The beam is then again refracted into the coupling fluid within the trailing wheel 22 to a forward-looking transducer 102 carried by the mounting yoke 70 in trailing wheel 22.

Transducers 100 and 102 are similar in size and construction but are aimed backward and forward, respectively, relative to the direction of travel of the inspection system. These two transducers 100 and 102 are mounted to be aimed at the same angle to the perpendicular to surface 13, e.g. 20°, to provide a symmetrical propagation path for the ultrasonic beam U1. The two transducers are each used in turn as a sender and a receiver, and preferably their roles are switched every cycle, i.e. the transmitter becomes the receiver and vice versa on alternate cycles. The received signal amplitude is monitored and if any defects lie in the path of the ultrasonic beam in the test material, a corresponding drop in amplitude would be detected. This arrangement is ideally suited for the inspection of welds in welded rails since the response is dependent less on defect orientation than on defect size. The transducers 100 and 102 are oriented with respect to the perpendicular to provide an ultrasonic beam which is emitted into the test material at a resultant angle of about 40° to the perpendicular to surface 13. To provide this resultant angle in a test material of steel from a wheel filled with a mixture of 60% water and 40% ethylene glycol, the transducers 100 and 102 are each oriented to transmit a beam in the liquid at an angle of about 20° to the perpendicular to the rail surface 13. The liquid may contain corrosion inhibitors. Other anti-freeze solutions may be used, such as pure ethylene glycol, in which event the velocity of sound propagation in the liquid may be somewhat different from the present example, and thus the particular angles at which the transducers are aimed are slightly changed. Also, changes in temperature slightly change the propagation velocities and angular relationships.

It will be observed that the orientation angle of transducers 100 and 102 is dependent upon the spacing distance d between the leading and trailing wheels 20 and 22 and the thickness t of the test material. This adjustment is desirable since the height of a railroad rail is proportionate to its weight. It is not uncommon for railroads to have several tracks incorporating varying heights. For example, a main line rail may weigh approximately 125 pounds per yard of length, a heavy traffic line rail may weigh approximately 140 pounds per yard of length, and a spur line track may weigh approximately 72 pounds per yard of length, and other weights and sizes of rail are also used.

So that the transducers may be fixedly mounted to yokes 70, and so that substantially a 40° propagation angle in the test material may be maintained for different thicknesses "t" of test material, motor 34 is operated to cause lead screw 32 to adjust the spacing d between the wheels. Preferably, the spacing d is adjusted automatically through a servo-control 104 for the motor 34 which responds to a thickness measuring means 106. This thickness monitoring means as shown by the dashed connection line 107 serves to monitor one of the so-called "zero degree" transducers 110, as shown (or 108, if desired). These zero degree transducers 110 and 108 are aimed virtually straight down, and thus the time required for the vertical ultrasonic beam U2 have to travel down through the rail being tested and to be reflected from the bottom surface 17 and to travel back up to the top surface 13 indicates the exact height of the rail. The thickness measurement means 106 measures this rail height "t," and the servo control 104 then automatically adjusts the spacing "d" in accordance with the height of the rail line being tested.

It is preferred that the mode of vibration utilized for testing in the steel rail be the shear wave mode. There is longitudinal sound wave transmission and shear wave sound transmission in steel. The longitudinal is a much faster sound transmission mode having a velocity of approximately 5,900 meters per second and thus has a longer wavelength. This longer wavelength provides less resolution in searching for rail defects. Conversely, the shear wave (also called transverse wave) mode is slower transmission velocity of about 3,200 meters per second and thus has a resultant shorter wavelength. Therefore, the shear wave mode provides a greater resolution so as to enable smaller defects in the rail to be found. It is to be noted that when the shear wave beam is refracted to be travelling at an angle of approximately 35° or more to the perpendicular, then the longitudinal wave is refracted to an angle of 90° or more to be perpendicular and thus becomes a surface wave proceeding along the top surface 13 and is thereby dissipated. It is to be noted that the liquid within the wheels 20 and 22 is not capable of supporting a shear wave mode of sound transmission. Thus, there occurs a mode conversion from longitudinal to shear wave as the ultrasonic vibrational energy enters the rail from the liquid and there is the reverse mode conversion from shear wave to longitudinal wave as the ultrasonic vibrational energy enters the liquid from the rail.

Generally speaking, it is not desirable to use an angle much larger than 70° within the steel rail, because more than 70° unduly magnifies the effect of changes in velocity in the liquid upon changes in the angle of beam direction in the steel.

Preferably, the leading and trailing wheels 20 and 22 have zero degree transducers 108 and 110 which are oriented to emit beams U2 of ultrasonic energy downward perpendicularly through Teflon (polytetrafluoroethylene) waveguides 109 and 111 (FIGS. 2 and 3) to surface 13 into the test material. The downward-looking (zero degree) transducers 108 and 110, used in a pulse echo mode, can indicate whether there is a head and web separation, and can indicate the presence of bolt holes, bolt hole cracks, and some vertical split heads that occur in the web region. It is to be noted that these zero degree transducers 108 and 110 are mounted high up within the wheel. This location advantageously provides a long travel path of at least two inches within the wheel, which avoids problems of undesired echoes interfering with the reflected energy U2 returning from the bottom 17 of the test material M. The Teflon waveguides 109 and 111 serve to reduce beam divergence and thus also eliminate false echoes. In addition, by monitoring the time it takes for ultrasonic energy to be transmitted to the bottom surface 17 of the test material and reflected back to the transducer 108 or 110, as mentioned above, a measurement of thickness can be obtained and, therefore, as shown in FIG. 1, the ultrasonic transducer such as 110 may be used to supply a signal to the thickness measurement means 106.

The leading wheel 20 further carries an array of three horizontally spaced transducers 112, 114 and 116 oriented to send a beam of ultrasonic energy U3 forwardly into the length of test material M and substantially longitudinally therein, e.g. at a resultant angle of 70° to the perpendicular to the upper surface 13 of the test material. To provide a resultant angle of 70° in steel, from a 60% water-40% glycol mixture, the transducers 112, 114 and 116 are oriented to emit a beam at an angle of about 28° to 30° to the perpendicular. In a similar manner, trailing wheel 22 is provided with a horizontally spaced array of three transducers 118, 120 and 122 oriented to send a beam U4 of ultrasonic energy in a rearward direction at a resultant angle of about 70° to the perpendicular. One particular arrangement for the arrays of ultrasonic transducers 112, 114 and 116 and 118, 120, 122 which is very useful for rail testing comprises active elements with face dimensions of ½" diameter spaced by a center-to-center distance of ⅝". By spacing the transducers so that they emit the beam through a path distance s from the upper surface 13 of the test material with s being substantially the near field distance N of the ultrasonic beam, as calculated using standard formulas, then the diverging ultrasonic beam from the array of transducers provides substantially 100% lateral coverage of the rail head 12 at a distance of about 3" in front of the wheel (FIGS. 7 and 8).

Figure 7:
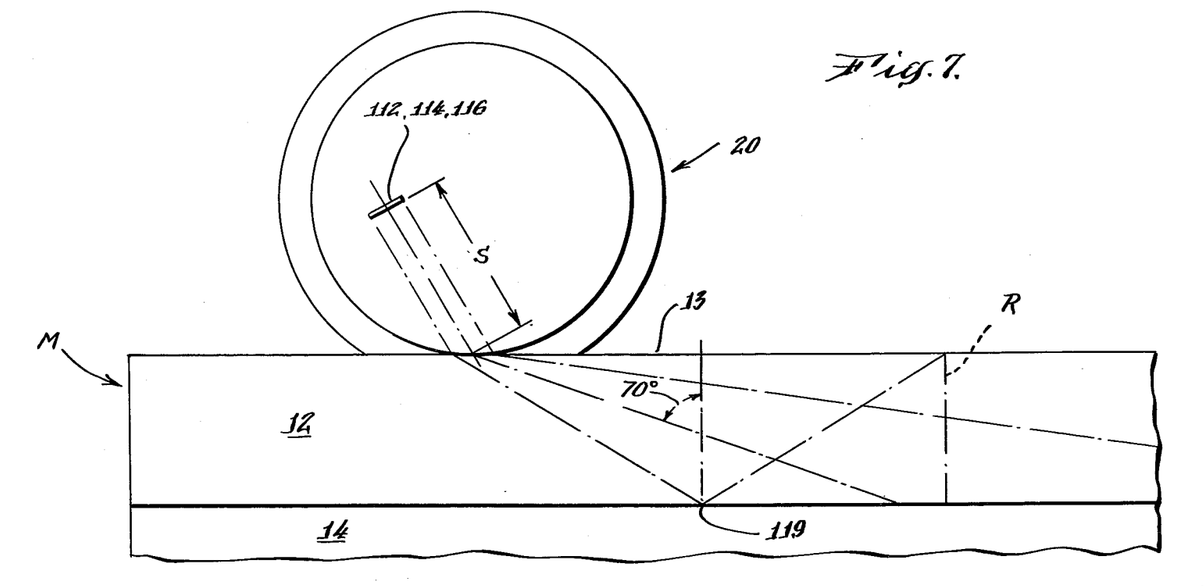
FIG. 7 is a diagrammatic side view showing the coverage of the longitudinally-looking ultrasonic beam.
Figure 8:
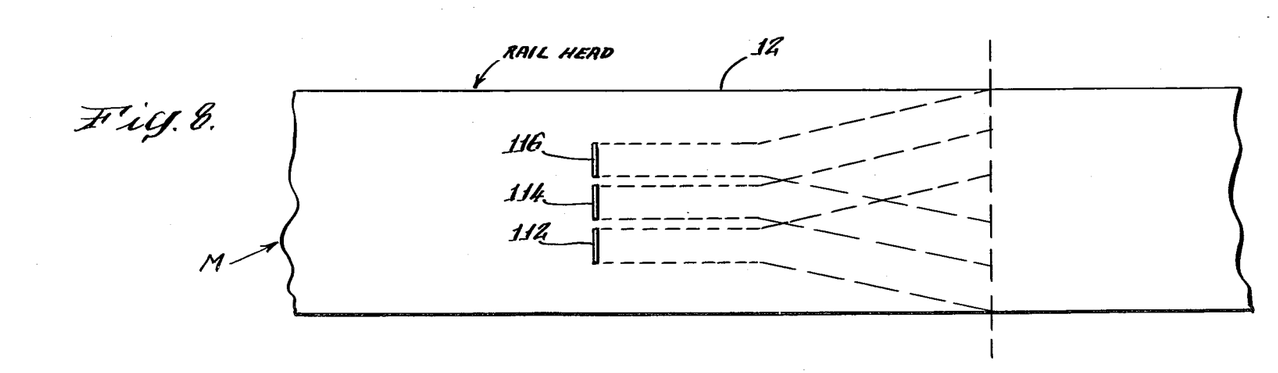
FIG. 8 is a diagramatic plan view showing the coverage of the longitudinally-looking ultrasonic beam.

As shown in FIG. 7, the diverging beam fills the entire cross-sectional area of the rail head in the region R at a distance of about 6 inches from the location of the bottom of the test wheel. This occurs by virtue of the reflection at 119 from the lower surface of the rail head.

In effect, by utilizing three transducers each having a small active area of about 0.20 square inches, i.e. approximately 12.7 mm in diameter, the near and far field effects are being manipulated. The result is to provide a shorter near field which terminates near the refracting interface contact surface at the bottom of the wheel. Thus, a greater divergence of the far field is produced within the rail head. Accordingly, transverse defects that occur anywhere within the head area can be detected. As a typical example, the near field distance N of a beam of ultrasonic energy of a frequency of 2.25 Megahertz in a mixture of 60% water and 40% ethyl glycol is about 2.16 inches, as calculated according to the formula:

$$N = 0.25\, D^2 f/c$$

where D = diameter = 12.7 mm. of the active surface of the transducer
f = sound frequency = $2.25 \times 10^6$
c = sound velocity = 1675 meters per second at room temperature As shown in FIG. 1, the transducers 100, 102, 108 and 110 are spaced along their emission paths from the refracting interface at the surface 13 of test material M by a distance which is substantially the near field distance of the ultrasonic beams emitted therefrom. This provides good coverage by the ultrasonic beams and accurate inspection of the test material.

Figure 6:
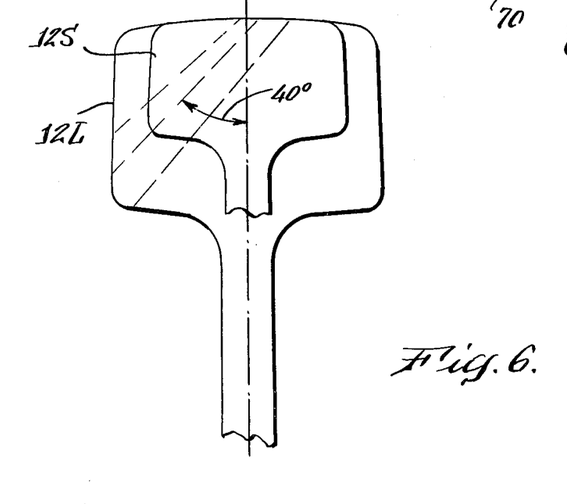
FIG. 6 is a sectional view through different superimposed rail sections showing the coverage of the side-looking ultrasonic beam.

In addition, the mounting yoke 70 of the leading wheel 20 carries a side-looking transducer 124 which emits a beam of ultrasonic energy toward the lower corner of the rail head 12 on the gauge side G of the rail, and trailing wheel 22 carries a side-looking transducer 126 which emits a beam of radiation toward the lower corner of the rail head 12 on the opposite or field side of the rail. The side-looking transducers 124 and 126 are oriented to emit a beam of ultrasonic energy into the test material at a resultant angle of about 40° to the perpendicular. Such an angle, as shown in FIG. 6, will be directed to the lower corner of a small rail head 12S and also to the lower corner of a large rail head 12L. As standard rails vary from 72 pounds per yard in weight to 140 pounds per yard in weight, with cross sections increasing accordingly, the testing system is able to accommodate all expected rail sizes. The side-looking transducers 124 and 126 are monitored for loss of amplitude of the reflection received back from the lower corner of the rail head. This indicates the presence of any vertical split head defect (which is a defect oriented parallel to the gauge and field side and would run longitudinally down the rail) which is a defect not heretofore reliably detected using ultrasonics.

By incorporation of a two-wheel test system 10 of twelve individually monitored transducers oriented as described above, the rail is essentially completely probed for the various kinds of defects that could lead to failures and possible derailments. This is accomplished by the sole use of ultrasonic energy, thereby eliminating the need of any supplementary equipment, such as magnetic induction systems which have traditionally limited testing speeds to a maximum of 8 miles per hour. The ultrasonic two-wheel inspection system 10, as described above, will allow testing in excess of 30 miles per hour thereby substantially reducing inspection costs per mile.

Inviting attention again to FIG. 5, it is noted that the spring washers 62, 64 push inwardly against a shoulder 130 on the axle 24 and push outwardly against the inner race 132 of the inner ball bearing 60. Then a snap ring 134 in a groove in the hub portion 56 anchors the outer race 136 of the inner ball bearing 60. The result is to tend to push the inner race 132 inward (to the left) while the outer race 136 relatively is pushed to the right. This pre-loading of the bearing 60 creates a canted line of action 140 of pressure on each of the balls. Conversely, the other bearing 58 has its inner race 142 held by a snap ring 144 in a groove in the axle 24 while its outer race is held by the other snap ring 134. The resultant pre-loading on the bearing 58 is thus in the opposite relative sense such that the line of action 150 of pressure on each of the balls is canted in the opposite direction. The relatively opposed sense of pre-loading of the respective races of a pair of bearings located side-by-side on the axle is advantageous in saving wear and tear. The vibration, wabble, or slap of the bearings, is prevented because they are each pre-loaded in a predetermined sense. There is no opportunity for the balls to "hunt" as they roll around in their races. They are forced to track true. The result in actual practice is to give a significantly increased operating life and to allow these relatively small diameter wheels to roll along precisely without bearing vibration up to 30 miles per hour or more.

Although a specific embodiment of the invention has been disclosed herein in detail, it is to be understood that this is for the purpose of illustrating the invention and should not be construed as necessarily limiting the scope of the invention since it is apparent that many changes can be made to the disclosed structures by those skilled in the art to suit particular applications.

I claim:

1. In a system of the type for performing ultrasonic inspection of a length of test material, such as a rail, with ultrasonic transducing means emitting a beam of ultrasonic energy from within sealed wheel means containing a coupling fluid therein and having a flexible cylindrical surface member transparent to the ultrasonic beam and arranged for rolling contact along the test material, the improvement which comprises:
   leading wheel means arranged for rolling contact along the length of test material;
   trailing wheel means spaced behind the leading wheel means and arranged for rolling contact along the length of test material; and
   ultrasonic transducer means fixedly mounted and oriented in each of the leading and trailing wheel means so that a beam of ultrasonic energy emitted from the transducer means in one wheel means will enter the test material, be reflected from the bottom surface thereof, and be received by the transducer means in the other wheel means;
   means for adjusting the spacing between said wheel means;
   means for measuring the thickness of the length of test material; and
   means for controlling said adjustment means in response to said measuring means to space said wheel means and orient said ultrasonic transducer means properly for the measured thickness of the test material;
   whereby the testing system provides improved detection of defects in the test material.

2. A system for performing ultrasonic inspection as claimed in claim 1 wherein the transducer means in each of the leading and trailing wheel means alternately transmit and receive ultrasonic energy.

3. A system for performing ultrasonic inspection as claimed in claim 1 wherein the ultrasonic transducer means in each of the leading and trailing wheel means is disposed to emit a beam of ultrasonic energy into the test material at an angle of about 40° from the perpendicular to the upper surface of the test material.

4. A system for performing ultrasonic inspection as claimed in claim 1 wherein the ultrasonic transducer means in each of the leading and trailing wheel means is spaced from the upper surface of the test material by substantially the near field distance of the beam of ultrasonic energy.

5. A system for performing ultrasonic inspection as claimed in claim 1 wherein the means for measuring the thickness of the test material comprises additional ultrasonic transducer means positioned to emit a beam of ultrasonic energy substantially perpendicularly to the upper surface of the test material.

6. A system for performing ultrasonic inspection as claimed in claim 1 wherein the means for controlling the adjusting means comprises a servomechanism.

7. A system for performing ultrasonic inspection as claimed in claim 1 further comprising side-looking ultrasonic transducer means in at least one of the leading and trailing wheel means for emitting a beam of ultrasonic energy into the test material transversely to the direction of wheel travel.

8. A system for performing ultrasonic inspection as claimed in claim 7 wherein the side-looking ultrasonic transducer means emit a beam of ultrasonic energy into the test material at a resultant angle of about 40° to the perpendicular to the upper surface of the test material.

9. A system for performing ultrasonic inspection as claimed in claim 7 wherein the side-looking ultrasonic transducer means are spaced from the upper surface of the test material by substantially the near field distance of the ultrasonic beam.

10. A system for performing ultrasonic inspection as claimed in claim 7 wherein the side-looking ultrasonic transducer means are in both wheel means.

11. A system for performing ultrasonic inspection as claimed in claim 10, wherein the side-looking transducer means in the leading wheel means emits a beam of ultrasonic energy to one side, and the side-looking transducer means in the trailing wheel means emits a beam of ultrasonic energy to the other side.

12. A system for performing ultrasonic inspection as claimed in claim 1 wherein at least one of the wheel means has normal-looking ultrasonic transducer means positioned to emit a beam of ultrasonic energy substantially perpendicularly to the upper surface of the test material.

13. A system for performing ultrasonic inspection as claimed in claim 12 wherein said normal-looking ultrasonic transducer means is spaced from the upper surface of the test material by substantially the near field distance of the ultrasonic beam.

14. A system for performing ultrasonic inspection as claimed in claim 12 wherein said normal-looking ultrasonic transducer means are in each of the leading and trailing wheel means.

15. In a method for performing ultrasonic inspection of a length of test material, such as a rail, with ultrasonic transducing means emitting a beam of ultrasonic energy from within sealed wheel means containing a coupling fluid therein and having a cylindrical surface transparent to the ultrasonic beam and arranged for rolling contact along the test material, the improvement which comprises:
providing leading and trailing wheel means;
emitting a send-receive beam of ultrasonic energy from transducer means in one of the wheel means;
reflecting the send-receive beam of ultrasonic energy from the bottom of the test material;
receiving the send-receive beam of ultrasonic energy with transducer means in the other wheel means;
emitting a first transverse beam of ultrasonic energy into the test material from transducer means in the leading wheel means transversely to the direction of travel thereof to one side; and
emitting a second transverse beam of ultrasonic energy into the test material from transducer means in the trailing wheel means transversely to the direction of travel thereof to the other side;
whereby detection of defects in the test material is improved.

16. A method for performing ultrasonic inspection as claimed in claim 15 further comprising transmitting a send-receiver beam of ultrasonic energy alternately from one wheel means to the other.

17. A method for performing ultrasonic inspection as claimed in claim 15 further comprising adjusting the spacing of the leading and trailing wheel means to accommodate different thicknesses of test material.

18. A method for performing ultrasonic testing as claimed in claim 17 further comprising measuring the thickness of the test material and adjusting the spacing of the wheel means in accordance with the measured thickness.

19. A method for performing ultrasonic testing as claimed in claim 18 wherein the step of measuring thickness comprises transmitting a normal beam of ultrasonic energy substantially perpendicularly through the test material.

20. A method for performing ultrasonic inspection as claimed in claim 15 wherein the step of emitting a beam of ultrasonic energy comprises emitting the send-receive beam a distance away from the surface of the test material which is substantially the near field distance of the ultrasonic beam.

21. A method for performing ultrasonic testing as claimed in claim 15 wherein the step of emitting a send-receive beam of ultrasonic energy comprises emitting the beam into the test material at a resultant angle of about 40° to the perpendicular to the upper surface of the test material.

22. A method for performing ultrasonic testing as claimed in claim 15 wherein the step of emitting a transverse beam comprises emitting the beam into the test material at a resultant angle of about 40° to the perpendicular to the surface thereof.

23. A method for performing ultrasonic testing as claimed in claim 15 wherein the step of emitting a transverse beam comprises emitting the beam a distance from the test material which is substantially the near field distance of the ultrasonic beam.

24. A method for performing ultrasonic testing as claimed in claim 15 further comprising emitting a normal beam of ultrasonic energy perpendicularly to the surface of the test material.

25. In a system of the type of performing ultrasonic inspection of a length of test material, such as a rail, with ultrasonic transducing means emitting a beam of ultrasonic energy from within sealed wheel means containing a coupling fluid therein and having a flexible cylindrical surface member transparent to the ultrasonic beam and arranged for rolling contact along the test material, the improvement which comprises:
leading wheel means arranged for rolling contact along the length of test material;
trailing wheel means spaced behind the leading wheel means and arranged for rolling contact along the length of test material;
send-receive ultrasonic transducer means oriented in each of the leading and trailing wheel means so that a beam of ultrasonic energy emitted from the send-receive transducer means in one wheel means will enter the test material, be reflected from the bottom surface thereof, and be received by the send-receive transducer means in the other wheel means;
first side-looking transducer means in said leading wheel means for emitting a beam of ultrasonic energy into the test material transversely to the direction of wheel travel to one side; and
second side-looking transducer means in said trailing wheel means for emitting a beam of ultrasonic energy into the test material transversely to the direction of wheel travel to the other side;
whereby the testing system provides improved detection of defects in the test material.

26. A system for performing ultrasonic inspection as claimed in claim 25 wherein the send-receive transducer means in each of the leading and trailing wheel means alternately transmit and receive ultrasonic energy.

27. A system for performing ultrasonic inspection as claimed in claim 25 wherein the send-receive ultrasonic transducer means in each of the leading and trailing wheel means is disposed to emit a beam of ultrasonic energy into the test material at a resultant angle of about 40° from the perpendicular to the upper surface of the test material.

28. A system for performing ultrasonic inspection as claimed in claim 25 wherein the send-receive ultrasonic transducer means in each of the leading and trailing wheel means is spaced from the upper surface of the test material by substantially the near field distance of the beam of ultrasonic energy.

29. A system for performing ultrasonic inspection as claimed in claim 25 wherein the send-receive ultrasonic transducer means in each of the leading and trailing wheel means are fixedly mounted, and wherein the system further comprises means for adjusting the spacing between the wheel means, whereby different thicknesses of test material may be tested.

30. A system for performing ultrasonic inspection as claimed in claim 29 further comprising means to measure the thickness of a length of test material and for controlling the means for adjusting the wheel spacing in response thereto to orient the send-receive ultrasonic transducer means properly for that thickness of test material.

31. A system for performing ultrasonic inspection as claimed in claim 30 wherein the means for measuring the thickness of the test material comprises additional normal-looking ultrasonic transducer means positioned to emit a beam of ultrasonic energy substantially perpendicularly to the upper surface of the test material.

32. A system for performing ultrasonic inspection as claimed in claim 30 wherein the means for controlling the adjusting means comprises a servomechanism.

33. A system for performing ultrasonic inspection as claimed in claim 25 wherein the side-looking ultrasonic transducer means emit a beam of ultrasonic energy into the test material at a resultant angle of about 40° to the perpendicular to the upper surface of the test material.

34. A system for performing ultrasonic inspection as claimed in claim 25 wherein the side-looking ultrasonic transducer means are spaced from the upper surface of the test material by substantially the near field distance of the ultrasonic beam.

35. A system for performing ultrasonic inspection as claimed in claim 25 wherein at least one of the wheel means has normal-looking ultrasonic transducer means positioned to emit a beam of ultrasonic energy substantially perpendicularly to the upper surface of the test material.

36. A system for performing ultrasonic inspection as claimed in claim 35 wherein said normal-looking ultrasonic transducer means is spaced from the upper surface of the test material by substantially the near field distance of the ultrasonic beam.

37. A system for performing ultrasonic inspection as claimed in claim 35 wherein said normal-looking ultrasonic transducer means are in each of the leading and trailing wheel means.

38. In a method for performing ultrasonic inspection of a length of test material, such as a rail, with ultrasonic transducing means emitting a beam of ultrasonic energy from within sealed wheel means containing a coupling fluid therein and having a cylindrical surface transparent to the ultrasonic beam and arranged for rolling contact along the test material, the improvement which comprises:

providing leading and trailing wheel means;

emitting a send-receive beam of ultrasonic energy from transducer means in one of the wheel means;

reflecting the send-receive beam of ultrasonic energy from the bottom surface of the test material;

receiving the reflected send-receive beam of ultrasonic energy with transducer means in the other wheel means;

measuring the thickness of the test material and continuously and automatically adjusting the spacing of the wheel means in accordance with the measured thickness to properly position said transducer means to emit and receive the beam of ultrasonic energy;

whereby detection of defects in the test material is improved.

39. A method for performing ultrasonic inspection as claimed in claim 38 further comprising transmitting a send-receive beam of ultrasonic energy alternately from one wheel means to the other.

40. A method for performing ultrasonic testing as claimed in claim 38 wherein the step of measuring thickness comprises transmitting a beam of ultrasonic energy substantially perpendicularly through the test material.

41. A method for performing ultrasonic inspection as claimed in claim 38 wherein the step of emitting a send-receive beam of ultrasonic energy comprises emitting the beam a distance away from the surface of the test material which is substantially the near field distance of the ultrasonic beam.

42. A method for performing ultrasonic testing as claimed in claim 38 wherein the step of emitting a send-receive beam of ultrasonic energy comprises emitting the beam into the test material at a resultant angle of about 40 degrees to the perpendicular to the upper surface of the test material.

43. A method for performing ultrsonic testing as claimed in claim 38 further comprising emitting a beam of ultrasonic energy transversely to the direction of travel of the wheel means.

44. A method for performing ultrasonic testing as claimed in claim 43 wherein the step of emitting a transverse beam comprises emitting the beam into the test material at a resultant angle of about 40 degrees to the perpendicular to the surface thereof.

45. A method for performing ultrasonic testing as claimed in claim 43 wherein the step of emitting a transverse beam comprises emitting the beam a distance from the test material which is substantially the near field distance of the ultrasonic beam.

46. A method for performing ultrasonic testing as claimed in claim 43 comprising emitting a transverse beam to one side of the leading wheel means, and to the other side from the trailing wheel means.

47. A method for performing ultrasonic testing as claimed in claim 38 further comprising emitting a beam of ultrasonic energy perpendicularly to the surface of the test material.

* * * * *

UNITED STATES PATENT AND TRADEMARK OFFICE
CERTIFICATE OF CORRECTION

PATENT NO. : 4,165,648

DATED : August 28, 1979

INVENTOR(S) : Dominick A. Pagano

It is certified that error appears in the above-identified patent and that said Letters Patent are hereby corrected as shown below:

Column 8, line 35 - Change "an" to -- a resultant --.

Signed and Sealed this

Twenty-ninth Day of January 1980

[SEAL]

Attest:

SIDNEY A. DIAMOND

Attesting Officer　　　Commissioner of Patents and Trademarks